United States Patent [19]

Cooper et al.

[11] Patent Number: 5,280,043
[45] Date of Patent: Jan. 18, 1994

[54] SULPHONAMIDO CONTAINING PHENYLALKANOIC ACIDS AS THROMBOXANE $A_2$ ANTAGONISTS

[75] Inventors: David G. Cooper, Letchworth; Andrew D. Gribble, Woolmer Green, both of England

[73] Assignee: Smith Kline & French Laboratories Ltd., Welwyn Garden City, England

[21] Appl. No.: 862,161

[22] Filed: Apr. 2, 1992

Related U.S. Application Data

[63] Continuation of Ser. No. 416,901, Oct. 4, 1989, abandoned.

[30] Foreign Application Priority Data

Oct. 10, 1989 [GB] United Kingdom .............. 8823731.8

[51] Int. Cl.$^5$ ................... A61K 31/19; A61K 31/235; A61K 31/18
[52] U.S. Cl. ..................................... 514/562; 514/539; 514/603; 514/604; 560/12; 562/430; 564/91
[58] Field of Search ............................ 560/12; 562/430; 514/539, 562, 603, 604; 564/91

[56] References Cited

U.S. PATENT DOCUMENTS 4,258,058  3/1981  Witte et al. ..................... 560/12 X
4,443,477  4/1984  Witte et al. ..................... 560/12 X

FOREIGN PATENT DOCUMENTS 0223593  5/1984  European Pat. Off. .
0239907  3/1987  European Pat. Off. .
0194548  9/1987  European Pat. Off. .
0255728  2/1988  European Pat. Off. .
3535167  4/1987  Fed. Rep. of Germany .

OTHER PUBLICATIONS

*Chemical Abstracts*, vol. 105, No. 11, 97029p, (1986).
Coutts et al., *J. Chem. Soc. Perkin Trans.* 1, pp. 1829–1836, (1985).

*Primary Examiner*—José G. Dees
*Assistant Examiner*—Vera C. Clarke
*Attorney, Agent, or Firm*—Dara L. Dinner; Stephen Venetianer; Edward T. Lentz

[57] ABSTRACT

Phenylalkanoic acids containing a sulphonamido group, and their use in a method of treatment of thromboxane-$A_2$ mediated diseases are disclosed. A compound of the invention is 4-[4-(phenyl-sulphonamido)phenyl]butyric acid.

11 Claims, No Drawings

SULPHONAMIDO CONTAINING PHENYLALKANOIC ACIDS AS THROMBOXANE A₂ ANTAGONISTS

This is a continuation of application Ser. No. 07/416,901, filed Oct. 4, 1989, now abandoned.

The present invention relates to a class of phenylalkanoic acid compounds containing a sulphonamido group which have activity as thromboxane $A_2$ antagonists, to the use of the compounds in medicine, to pharmaceutical compositions containing them and to methods for their preparation.

Thromboxane $A_2$ ($TXA_2$) is a potent vasoconstricting and platelet aggregating agent which is formed in platelets and other tissues as a product of the "arachidonic acid cascade". $TXA_2$ is produced by the thromboxane synthetase catalysed conversion of prostaglandin $H_2$ ($PGH_2$) which in turn is produced, via the intermediacy of prostaglandin $G_2$ ($PGG_2$), by the action of cyclooxygenase on arachidonic acid. The potency of $TXA_2$ is such that very small amounts can trigger serious biological consequences and it has been implicated in mediating pathophysiological actions in severe disorders such as circulatory shock and myocardial ischaemia.

One method of inhibiting the effects of thromboxane $A_2$ is through the selective antagonism of $TXA_2/PGH_2$ at the receptor level and various compounds have been reported as $TXA_2$ receptor antagonists, see for example U.S. Pat. No. 4,536,510 and U.S. Pat. No. 4,443,477.

The present invention provides a compound of the formula (I):

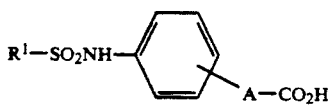
(I)

and salts, esters and amides thereof, wherein $R^1$ is phenyl optionally substituted by one or more substituents chosen from halogen, $C_{1-4}$alkyl, $C_{1-6}$acyl, $C_{1-4}$alkoxy, nitro and trifluoromethyl; and A is an acyclic hydrocarbon group having from 2 to 8 linear carbon atoms, particularly 2 to 6 carbon atoms and preferably 2 to 4 carbon atoms.

By linear carbon atoms is meant those carbon atoms extending in an unbranched chain between the phenylene ring and the carboxyl group. Each linear carbon atom can be substituted by one or two $C_{1-2}$alkyl substituents, preferably methyl substituents. It is preferred that the total number of carbon atoms in the group A does not exceed 10.

Particular groups A are $(CH_2)_3$, $(CH_2)_4$, $(CH_2)_2C(CH_3)_2$ and $(CH_2)_3C(CH_3)_2$, a preferred group being $(CH_2)_3$.

$R^1$ is suitably an unsubstituted phenyl group or, more suitably a phenyl group substituted by one or two substituents, preferably one of which is located at the 4-position of the phenyl ring.

Particular substituents are bromine, chlorine, methyl, methoxy, trifluoromethyl and nitro, particularly preferred substituents being bromine and chlorine.

Preferred groups $R^1$ include 4-chlorophenyl and 4-bromophenyl.

The group A-CO₂H can be ortho, meta or para with respect to the group $R^1SO_2NH$ but particularly it is in the para position.

Preferred compounds of the present invention are
4-[4-(phenylsulphonamido)phenyl]butyric acid;
4-[4-(4-chlorophenylsulphonamido)phenyl]butyric acid;
4-[4-(4-bromophenylsulphonamido)phenyl]butyric acid;
4-[4-(4-methylphenylsulphonamido)phenyl]butyric acid;
4-[4-(4-methoxyphenylsulphonamido)phenyl]butyric acid;
2,2-dimethyl-4-[4-(4-methylphenylsulphonamido)phenyl]-butyric acid;
2,2-dimethyl-4-[4-(4-chlorophenylsulphonamido)phenyl]-butyric acid;
2,2-dimethyl-4-[4-(4-bromophenylsulphonamido)phenyl]-butyric acid;
2,2-dimethyl-4-[4-phenylsulphonamido)phenyl]butyric acid; and
2,2-dimethyl-4-[4-(4-methoxyphenylsulphonamido)phenyl]-butyric acid;
and pharmaceutically acceptable salts thereof.

Compounds of the formula (I) can form carboxylate salts and salts of the sulphonamide group.

Examples of carboxylate salts are alkali metal, alkaline earth metal and ammonium salts. Alkali and alkaline earth metal salts typically are formed by interaction of a carboxylic acid with a metal alkoxide or hydroxide whereas ammonium salts typically are formed by interaction of the carboxylic acid with the appropriate amine or the appropriate ammonium hydroxide.

It is preferred that the salts are pharmaceutically acceptable, although non-pharmaceutical salts are also within the scope of the invention. Such salts can be converted into pharmaceutically acceptable salts or into the corresponding free base or free acid.

Where the compounds of formula (I) exist as solvates, for example hydrates and alcoholates, such forms are also within the scope of the invention.

Compounds of the formula (I) can be prepared by the reaction of a compound of the formula (II):

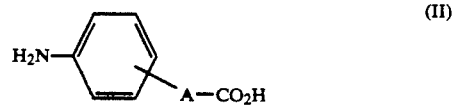
(II)

or a carboxylate salt, amide or ester thereof, with a compound $R^1SO_2L$ where L is a leaving group displaceable by amino.

Examples of leaving groups L are the halogens, particularly chlorine.

The reaction of compounds of the formula (II) with compounds of the formula $R^1SO_2L$ can be conducted under conditions known for the preparation of analogous sulphonamides. Thus, for example, the reaction can be conducted in a solvent, for example benzene, toluene or a polar solvent such as acetone, acetonitrile, a halogenated hydrocarbon such as dichloromethane or a basic solvent such as pyridine, with heating where required, for example at the reflux temperature of the solvent. Where the solvent is non-basic the reaction typically is conducted in the presence of a base such as pyridine or a trialkylamine such as triethylamine.

Alternatively, the reaction can be conducted under Schotten-Baumann conditions, i.e. the reactants are stirred or shaken together in the presence of an aqueous alkali such as dilute sodium hydroxide.

Compounds of the formula (II) can be prepared from a compound of the formula (III):

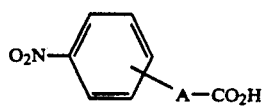

(III)

by treatment with an appropriate reducing agent, for example by hydrogenating over a transition metal catalyst such as palladium on charcoal, or by treatment with hydrazine in the presence of palladium on charcoal. Suitable solvents for use in such reactions are $C_{1-4}$alkanols such as methanol and ethanol and typically the reaction is conducted at approximately ambient temperature.

Compounds of the formula (I) are useful in the treatment of diseases in which $TXA_2$ is a factor. Thus they would be useful in the treatment of disorders in which aggregation of blood platelets and vasoconstriction play a part.

Particular clinical indications in which the present compounds would be of interest include the treatment or management of post myocardial infarction, coronary thromboses (e.g. in combination with tissue plasminogen activator and other thrombolytics), unstable angina, transient ischaemia, coronary artery bypass grafts, cardiac valve replacement and peripheral and vascular grafts including for example renal transplants.

The compounds of the formula (I) can be administered as the pure compound but it is more usual to administer them as part of a pharmaceutical composition in association with a carrier and one or more excipients. In a further aspect, therefore, the present invention provides a pharmaceutical composition comprising a compound of the formula (I) and a pharmaceutically acceptable carrier.

The compositions can be administered in standard manner, for example orally, parenterally, transdermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil. Such compositions can be administered, for example, by bolus injection or by infusion.

A typical suppository formulation comprises a compound of formula (I) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each such dosage unit suitably contains from 1 mg to 1 g, preferably from 5 mg to 500 mg, e.g. 100 mg or 200 mg, of a compound of the formula (I) or a pharmaceutically acceptable salt thereof calculated as the compound itself.

A typical daily dosage regimen is 10 mg to 1 g for an average human weighing approximately 70 kg, administered in 1 to 4 dosage units, preferably 1 or 2.

The compositions of this invention, in addition to containing a compound of the formula (I) can also contain other agents; for example one or more agents chosen from phosphodiesterase inhibitors, hypolipidaemic agents, platelet aggregation inhibitors, vasodilators, $\beta$-adrenergic receptor blockers, ACE inhibitors, tissue plasminogen activator and other thrombolytics, and antiarrhythmics.

The compositions of the present invention are prepared by bringing the active constituent into association with a pharmaceutically acceptable carrier and optionally other excipients and ingredients as defined above.

As indicated above, compounds of the formula (I) have biological activity that is indicative of an ability to antagonise $TXA_2$ receptors. The $TXA_2$ activity has been demonstrated in the human platelet binding assay.

The platelet binding assay used was essentially the method described by Mais et al, *J. Pharm. Exp. Ther.*, 1985, 235(3), 729–734 where [$^{125}$I]PTA-OH was used as the receptor ligand.

The $IC_{50}$ values represent the concentration which produces a 50% inhibition of specific [$^{125}$I]PTA-OH binding.

The compounds of Examples 1 to 4 had $IC_{50}$ values in the range of 0.02 to 0.6 $\mu$M in the platelet binding assay.

The following Examples are illustrative of the invention.

In the Examples, all temperatures are in °C. Melting points are uncorrected and were obtained in an open capillary tube using a Büchi 510 Melting Point Apparatus.

EXAMPLE 1

A. 4-(4-Aminophenyl)butyric acid

A mixture of 4-(4-nitrophenyl)butyric acid (3 g, 14 mmol) (Aldrich Chemical Company Ltd.) and 10% palladium on charcoal catalyst (0.3 g) in ethanol (100 ml) was submitted to gaseous hydrogen at 50 p.s.i., 20° C., for 30 minutes. The mixture was then filtered and concentrated. The resulting solid residue was recrystallised from isopropanol to give 4-(4-aminophenyl)-butyric acid. (1.9 g, 76%) mp. 125°-127° C.

B. 4-[4-(Phenylsulphonamido)phenyl]butyric acid

To a solution of 4-(4-aminophenyl)butyric acid (1 g, 5.6 mmol) in dry acetone (30 ml) was added dropwise a solution of benzenesulphonyl chloride (0.99 g) and pyridine (1.1 g) in dry acetone (10 ml). The mixture was heated at reflux for 3 hours, then concentrated in vacuo. The resulting oil was dissolved in dichloromethane (100 ml) and the solution was washed with 2N aqueous HCl (2×100 ml), followed by water (2×100 ml). The dichloromethane solution was extracted with 10% aqueous NaOH (2×50 ml), followed by water (2×50 ml), and these extracts were combined and stirred with dichloromethane (100 ml) while conc. HCl was added to adjust the pH of the mixture to 5. The layers were separated and the organic solution was dried (MgSO$_{04}$) and concentrated in vacuo. The resulting solid was recrystallised from isopropanol to give 4-[4-(phenyl-sulphonamido)phenyl]butyric acid. (1.03 g, 58%) mp. 128°-130° C.

$C_{16}H_{17}NO_4S$:
Found: C 60.19; H 5.47; N 4.31; S 10.00.
Requires: C 60.17; H 5.37; N 4.39; S 10.04

EXAMPLES 2 to 4

Using the method described in Example 1, the following compounds were prepared. In each case, the appropriate phenylsulphonyl chloride was obtained from a commercial source.

2. 4-[4-(4-Chlorophenylsulphonamido)phenyl]butyric acid;
melting point 150°-151° C.
Found: C 54.59; H 4.72; N 3.72; S 8.83 Cl 9.88.
Requires: C 54.31; H 4.56; N 3.96; S 9.06; Cl 10.02.

3. 4-[4-(4-Methoxyphenylsulphonamido)phenyl]-butyric acid;
melting point 176°-177° C.
Found: C 58.67; H 5.57; N 3.95; S 9.28.
Requires: C 58.40; H 5.48; N 4.01; S 9.18.

4. 4-[4-(4-Bromophenylsulphonamido)phenyl]butyric acid
melting point 168°-169° C.
Found: C 48.17; H 4.13; N 3.40; S 7.92; Br 20.33.
Requires: C 48.25; H 4.05; N 3.52; S 8.05; Br 20.06.

What is claimed Is;

1. A method of treating a thromboxane - A$_2$ mediated disease which comprises administering to a subject in need thereof an effective amount of a compound of formula (I):

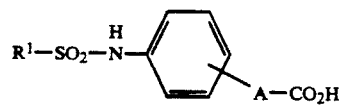

wherein
R$^1$ is phenyl optionally substituted by one or more substituents selected from the group consisting of halogen, C$_{1-4}$alkyl, C$_{1-6}$acyl, C$_{1-4}$alkoxy, nitro and trifluoromethyl; and
A is an acyclic hydrocarbon group having from 2 to 4 linear carbon atoms; and the pharmaceutically acceptable salts, esters, and amides thereof.

2. The method of treatment according to claim 1 in which the compound according to claim 1 is 4-[4-(phenylsulphonamido)phenyl]butyric acid or a pharmaceutically acceptable salt thereof.

3. The method of treatment according to claim 1 in which the compound is 4-[4-(4-chlorophenylsulphonamido)phenyl]butyric acid or a pharmaceutically acceptable salt thereof.

4. The method of treatment according to claim 1 in which the compound is 4-[4-(4-bromophenylsulphonamido)phenyl]butyric acid or a pharmaceutically acceptable salt thereof.

5. The method of treatment according to claim 1 in which the compound is 4-[4-(4-methylphenylsulphonamido)phenyl]butyric acid or a pharmaceutically acceptable salt thereof.

6. The method of treatment according to claim 1 in which the compound is 4-[4-(4-methoxyphenylsulphonamido)phenyl]butyric acid or a pharmaceutically acceptable salt thereof.

7. The method of treatment according to claim 1 in which the compound is 2,2-dimethyl-4-[4-(4-methylphenyl-sulphonamido)phenyl]-butyric acid or a pharmaceutically acceptable salt thereof.

8. The method of treatment according to claim 1 in which the compound is 2,2-dimethyl-4-[4-(4-chlorophenyl-sulphonamido)phenyl]butyric acid or a pharmaceutically acceptable salt thereof.

9. The method of treatment according to claim 1 in which the compound according to claim 15 is 2,2-dimethyl-4-[4-(4-bromophenyl-sulphonamido)phenyl]-butyric acid or a pharmaceutically acceptable salt thereof.

10. The method of treatment according to claim 1 in which the compound is 2,2-dimethyl-4-[4-(phenylsulphonamido)phenyl]-butyric acid or a pharmaceutically acceptable salt thereof.

11. The method of treatment according to claim 1 in which the compound is 2,2-dimethyl-4-[4-(4-methoxyphenylsulphonamido)phenyl]-butyric acid or a pharmaceutically acceptable salt thereof.

* * * * *